US010008089B2

(12) United States Patent
Brown et al.

(10) Patent No.: US 10,008,089 B2
(45) Date of Patent: Jun. 26, 2018

(54) PROVIDING AN ALERT TO A PERSON IN A DISTRESSED SITUATION

(71) Applicant: International Business Machines Corporation, Armonk, NY (US)

(72) Inventors: Michael Sean Brown, Wahroonga (AU); Stefan Harrer, Hampton (AU); Laurence J. Plant, North Balwyn (AU)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 38 days.

(21) Appl. No.: 15/195,994

(22) Filed: Jun. 28, 2016

(65) Prior Publication Data

US 2017/0372584 A1    Dec. 28, 2017

(51) Int. Cl.
*G08B 21/04* (2006.01)
*G10L 25/63* (2013.01)
*G08B 25/01* (2006.01)

(52) U.S. Cl.
CPC ....... *G08B 21/0453* (2013.01); *G08B 25/016* (2013.01); *G10L 25/63* (2013.01)

(58) Field of Classification Search
CPC .... G08B 21/0453; G08B 25/016; G10L 25/63
See application file for complete search history.

(56) References Cited

U.S. PATENT DOCUMENTS

| 8,630,820 B2 * | 1/2014 | Amis | G01S 19/16 455/404.1 |
| 9,300,799 B2 * | 3/2016 | Brown | H04M 3/5116 |

(Continued)

FOREIGN PATENT DOCUMENTS

WO    2013163090 A1    10/2013

OTHER PUBLICATIONS

Television documentary, "Don't Panic, Surviving Extremes", <URL: http://www.abc.net.au/tv/programs/dont-panic-surviving-extremes/. From the broadcaster is not available. The substance of this documentary was in a specific example of how someone who was caught on a fence when a fire was nearby was panicking until their phone rang; they took the call and in doing so returned to a calmer state and could more easily free themselves from the fencing.

(Continued)

*Primary Examiner* — Sisay Yacob
(74) *Attorney, Agent, or Firm* — Law Offices of Ira D. Blecker, P.C.

(57) ABSTRACT

A system for providing an alert to a user which includes a sensor for sensing user data pertaining to a user's condition; and a non-transitory storage medium that stores instructions. Also included is a processor that executes the instructions to: monitor the user data from the sensor for predefined conditions, at least one predefined condition pertaining to a mental state of the user; autonomously evaluate the user data for the predefined conditions; autonomously identify the predefined condition that matches the user's condition; autonomously determine a predefined alert corresponding to the predefined condition and to the user's condition to interact with the user to calm the user; and autonomously administer the predefined alert to the user.

20 Claims, 5 Drawing Sheets

(56) References Cited

U.S. PATENT DOCUMENTS

| | | | |
|---|---|---|---|
| 9,472,080 B1* | 10/2016 | Guo | G08B 21/02 |
| 9,584,971 B1* | 2/2017 | Guo | G08B 21/02 |
| 9,622,037 B2* | 4/2017 | Guo | H04W 4/023 |
| 2003/0012344 A1 | 1/2003 | Agarwal et al. | |
| 2005/0085257 A1* | 4/2005 | Laird | A61B 5/04 |
| | | | 455/550.1 |
| 2008/0094230 A1* | 4/2008 | Mock | G08B 1/08 |
| | | | 340/573.4 |
| 2011/0046920 A1* | 2/2011 | Amis | G01S 19/16 |
| | | | 702/181 |
| 2013/0012153 A1 | 1/2013 | Brosson et al. | |
| 2014/0364751 A1* | 12/2014 | Dugan | A61B 5/0002 |
| | | | 600/508 |
| 2015/0288819 A1* | 10/2015 | Brown | H04M 3/5116 |
| | | | 379/45 |
| 2016/0071392 A1* | 3/2016 | Hankey | G08B 21/0446 |
| | | | 340/573.1 |
| 2017/0061759 A1* | 3/2017 | Guo | G08B 21/02 |
| 2017/0064508 A1* | 3/2017 | Guo | G08B 21/02 |

OTHER PUBLICATIONS

Ashraf Darwish et al., "Wearable and Implantable Wireless Sensor Network Solutions for Healthcare Monitoring", Published: May 26, 2011, all pages.

* cited by examiner

PROVIDING AN ALERT TO A PERSON IN A DISTRESSED SITUATION

BACKGROUND

The present exemplary embodiments pertain to emergency, disaster or medical situations which a person may encounter and more particularly, to providing an alert to the person in an effort to calm the person so that the person may more readily be able to handle the emergency, disaster or medical situation.

There are innumerable emergency, disaster or medical situations that a person may find himself/herself in. For example, such situations may include a car crash, a bike accident, a medical emergency such as a heart attack, a separation of a child from the child's caregiver, an avalanche, a fire, an earthquake, a fall or any other similar kind of event.

It is common in these situation to focus on the person by monitoring the condition of the person and then notifying support to supply the emergency, disaster or medical assistance to the person.

BRIEF SUMMARY

The various advantages and purposes of the exemplary embodiments as described above and hereafter are achieved by providing, according to an aspect of the exemplary embodiments, a system for providing an alert to a user comprising: at least one sensor for sensing user data pertaining to a user's condition; and at least one non-transitory storage medium that stores instructions; Also provided is at least one processor that executes the instructions to: monitor the user data from the at least one sensor for predefined conditions, at least one predefined condition pertaining to a mental state of the user autonomously evaluate the user data for the predefined conditions; autonomously identify the predefined condition that matches the user's condition; autonomously determine a predefined alert corresponding to the user's condition to interact with the user; and autonomously administer the predefined alert to the user.

According to another aspect of the exemplary embodiments, there is provided a computer implemented method for providing an alert to a user comprising: monitoring user data from the user for predefined conditions, at least one predefined condition pertaining to a mental state of the user; autonomously evaluating the user data for the predefined conditions; autonomously identifying the predefined condition that matches the user's condition; autonomously determining a predefined alert corresponding to the user's condition to interact with the user; and autonomously administering the predefined alert to the user.

According to a further aspect of the exemplary embodiments, there is provided a computer program product for providing an alert to a user comprising a computer readable storage medium having program instructions embodied therewith, the program instructions executable by a processor to cause the processor to perform a method comprising: monitoring user data from the user for predefined conditions, at least one predefined condition pertaining to a mental state of the user; autonomously evaluating the user data for the predefined conditions; autonomously identifying the predefined condition that matches the user's condition; autonomously determining a predefined alert corresponding to the user's condition to interact with the user; and autonomously administering the predefined alert to the user.

BRIEF DESCRIPTION OF SEVERAL VIEWS OF THE DRAWINGS

The features of the exemplary embodiments believed to be novel and the elements characteristic of the exemplary embodiments are set forth with particularity in the appended claims. The Figures are for illustration purposes only and are not drawn to scale. The exemplary embodiments, both as to organization and method of operation, may best be understood by reference to the detailed description which follows taken in conjunction with the accompanying drawings in which:

DETAILED DESCRIPTION

When people are in a high stress, high adrenaline situation such as a natural disaster or a medical emergency, they sometimes need an external interrupt to refocus on a problem solving activity or an automatic response has to be triggered. Distressed situation management is often focused on a combination of coordinating and optimizing the response from emergency services, in combination with providing information and guidance to the general public. An area that is overlooked, but may also contribute to safety of people and property, is helping members of the general public through high adrenaline and medical emergency situations.

The exemplary embodiments are proposed (1) to proactively interact with the person in distress in addition to optionally providing a warning sign to a third party, (2) to provide an advanced cognitive analytics platform to analyze multiple factors in real-time and to determine an appropriate response to the person in distress, and (3) to go through a closed feedback loop for monitoring, analyzing and responding until a more stable state of the person in distress has been reached.

In the following description of the exemplary embodiments, "person" and "user" may be used interchangeably.

The exemplary embodiments include a system that may have some or all of the following components:

a wearable device(s) monitoring a user's vital signs and biometric parameters and environmental parameters;

a cognitive system analyzing the user's vital signs and biometric parameters and environmental parameters;

a mobile response system which can interact with the user; and a local emergency broadcast signal.

Figure 1:
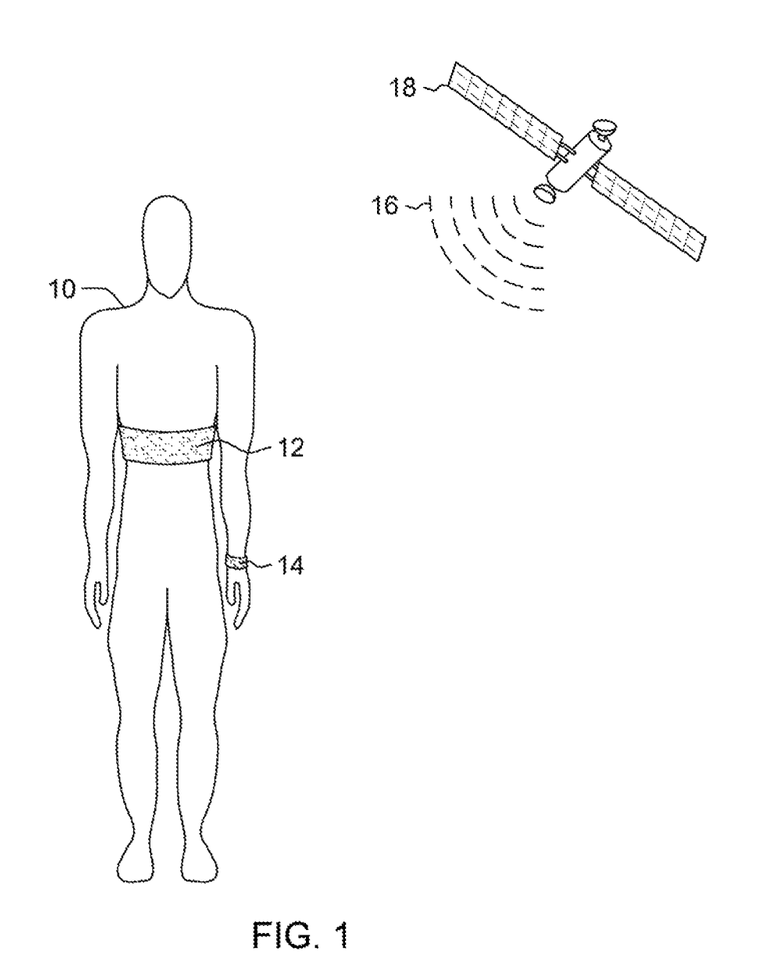
FIG. 1 is an illustration of a user having wearable devices including a chest band and a wrist band.

Referring to the drawings in more detail, and particularly referring to FIG. 1, there is illustrated a user 10 having one or more wearable devices 10, 12. For the purpose of illustration and not limitation, the user 10 may be wearing wearable devices such as a chest band 12 and a wrist band 14. Other wearable devices may include but not be limited to smart watches, head bands, fitness trackers, tattoo sensors and implants and wearable Bluetooth devices.

The wearable devices 12, 14 may have sensors to monitor the user's vital signs and biometric parameters such as pulse, blood pressure and body temperature. Other vital signs and biometric parameters may include the user's rate of movement, respiration rate, skin conductivity, pupil dilation and feedback from embedded devices such as a heart pace maker.

The wearable devices 12, 14 may further include the capability to communicate with other devices by, for example, cellular telephone, satellite, short range radio such as Bluetooth and WiFi. FIG. 1 illustrates one exemplary embodiment in which the wearable devices 12, 14 are receiving a signal 16 from a satellite 18. The wearable devices 12, 14 may have the reciprocal capability to transmit to another device (not shown) via the satellite 18 or any other communication means.

Figure 2:
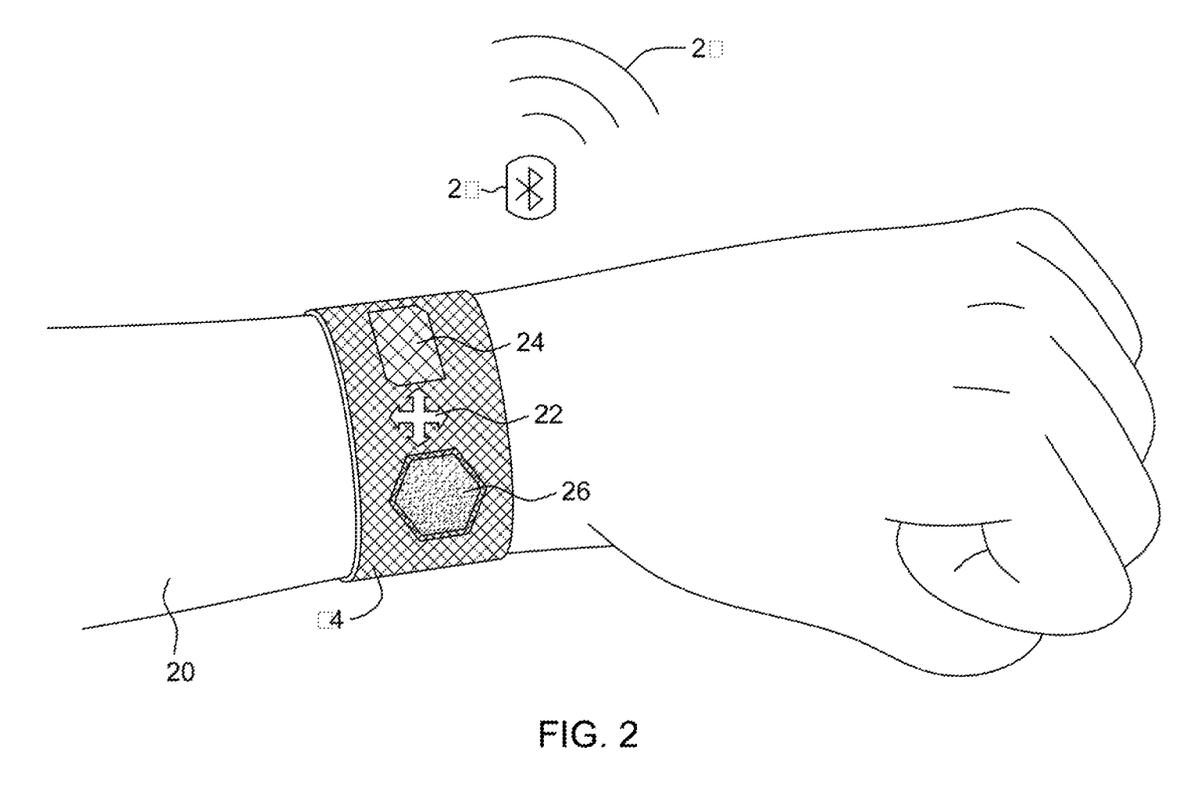
FIG. 2 is an illustration in more detail of a user having a wrist band.

FIG. 2 illustrates one exemplary embodiment of the wearable wrist band 14 which may fit on the wrist 20 of the user 10. The wrist band 14 may have the sensors to monitor any or all of the vital signs, biometric parameters and environment parameters mentioned previously. Particularly shown in FIG. 2, for the purpose of illustration and not limitation, is an accelerometer sensor 22 to monitor the rate of movement of the user 10. In one situation, the lack of movement of the user as indicated by the accelerometer sensor 22 in conjunction with the lack of a pulse rate may indicate the user may have had a heart attack.

In addition, the wearable device 14 may include a microphone 24 and a speaker 26 which may enable two way communication with a cognitive system to be discussed in more detail hereafter.

FIG. 2 further illustrates that the wearable wrist band 14 may have Bluetooth short range radio capability 27 or other communication capability 29.

The wearable chest band 12, or another wearable device, if present, may contain similar sensors and capabilities as described with respect to the wearable wrist band 14. In addition, the communication capability of the wearable devices 12, 14 allows the wearable devices 12, 14 to communicate with environmental sensors to learn about events that may affect the user such as weather events, fires, earthquakes, etc.

Figure 3:
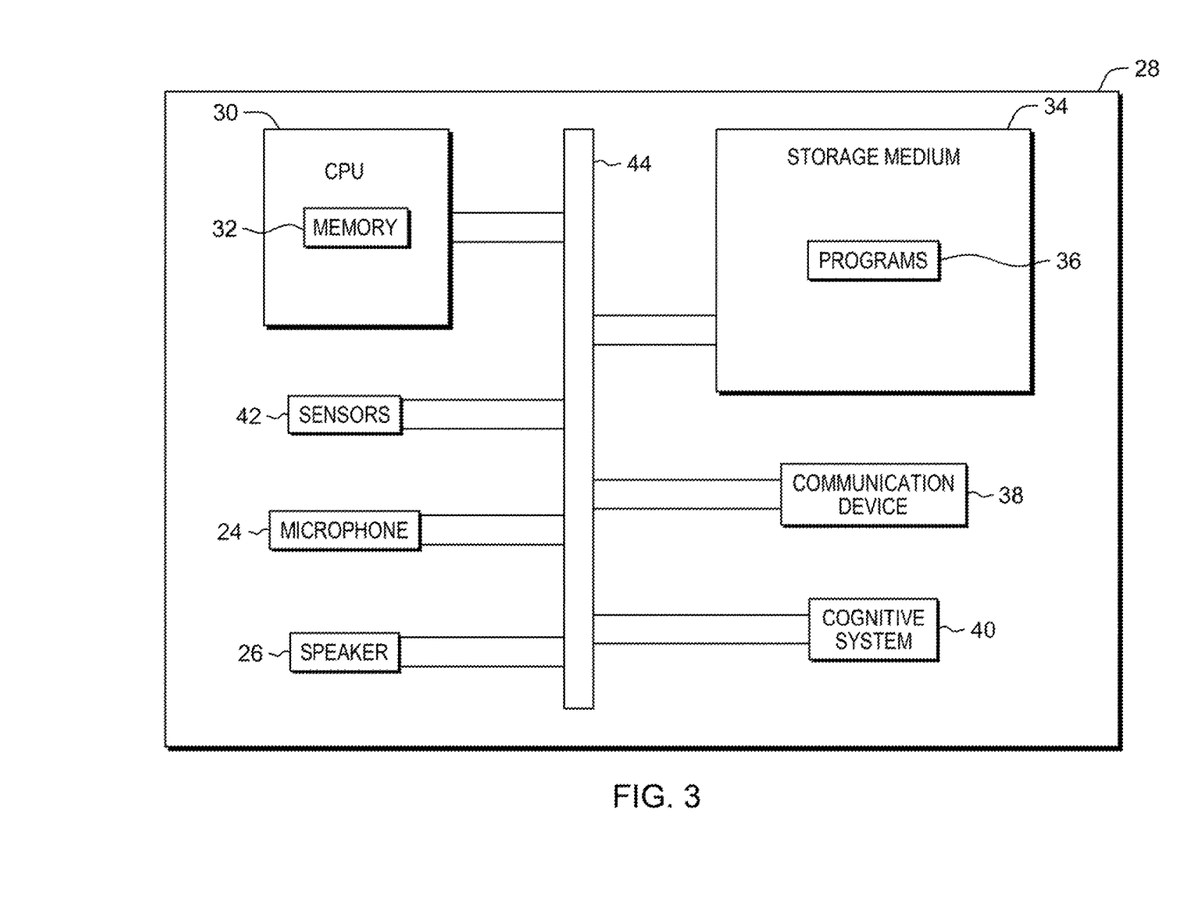
FIG. 3 is a block diagram of a computing device to be used in the exemplary embodiments.

Referring now to FIG. 3, there is illustrated an exemplary embodiment of a computing device 28 having a processor 30 (central processing unit (CPU)), memory 32 and non-transitory storage medium 34. Included within the storage medium 34 may be various programs 36. Computing device 28 may include one or more communication devices 38 to handle any of the communication capabilities mentioned previously such as cellular telephony, satellite transmission, Bluetooth short range radio and WiFi. Computing device 28 may further include the cognitive system 40. While the cognitive system 40 may be physically located within the computing device 28, it is also within the scope of the exemplary embodiments for the cognitive system 40 to be located remotely since the wearable devices 12, 14 have a communication capability which would enable contact with a remote computing system hosting the cognitive system 40.

In addition, the computing device 28 may have the capability to communicate with the sensors 42 mentioned previously (i.e., sensors to monitor any or all of the vital signs, biometric parameters and environment parameters), the microphone 24 and speaker 26. Providing connection to all the components of the computing device 28 may be a bus 44 in the computing device 28.

In one exemplary embodiment, the computing device 28 may be embedded in the wearable devices 12, 14. In another exemplary embodiment, the computing device 28 may be separate from the wearable devices 12, 14 such as in a smartphone or other electronic device carried by the user.

The wearable devices 12, 14 are essentially user interfaces which may provide interaction between the user wearing the wearable devices 12, 14 and the computing device 28.

Figure 4:
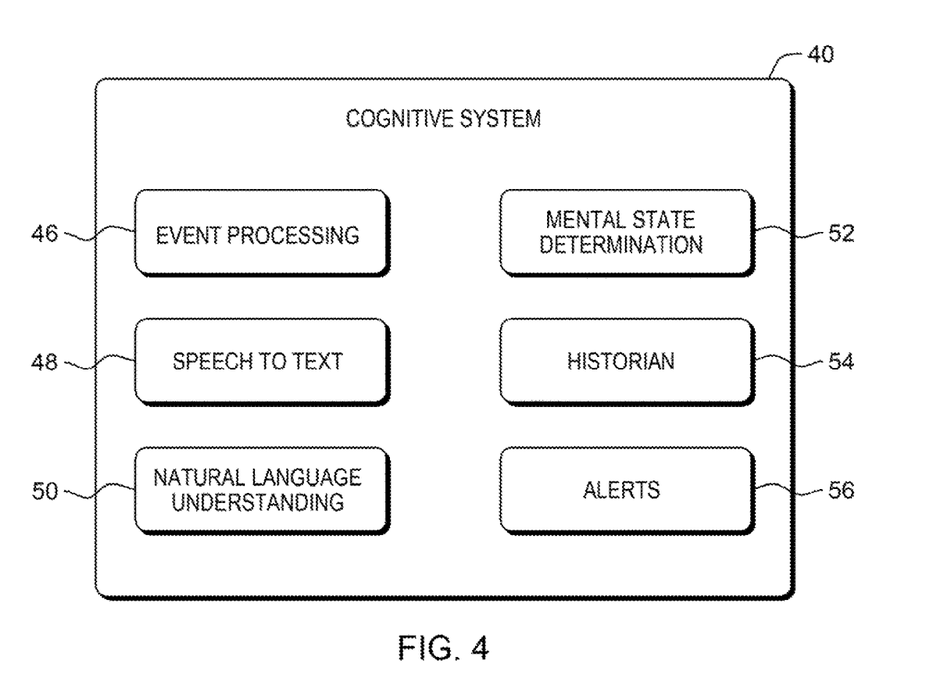
FIG. 4 is a block diagram of a cognitive system to be used in the exemplary embodiments.

The user interface of the exemplary embodiments includes the microphone 24, natural language speech synthesis within the cognitive system 40, the speaker 26 and notification alerts within the cognitive system 40. The user interface may also have a visual representation indicating that the wearable devices 12, 14 are engaged.

The microphone 24 may receive speech from the user into the wearable devices 12, 14.

The natural language speech synthesis may speak to the user through the speaker 26. The natural language speech synthesis may translate text to speech in order to speak to the user and relay the speech to the user via the speaker 26. The natural language speech synthesis may also translate into text the user's speech spoken into the microphone 24 and then interpreted so that the intent and meaning of the user's speech can be understood.

The notification alerts can include verbal commands, vibration or playing tones in order to secure the user's attention.

The cognitive system 40 is described in more detail in FIG. 4 and may include event processing 46, speech to text processing 48, natural language understanding 50, mental state determination 52, historian 54 and alerts 56.

The event processing 46 includes real time multi-event processing which analyzes and correlates event data from user sensors and environmental sensors.

The speech to text 48 converts speech from the user that is spoken into the microphone 24 into text to establish a record in text format of what the user is saying. The speech to text 48 may provide an additional function to translate text alerts into speech and provide the speech to the user through the speaker 26.

The natural language understanding 50 receives the input from the speech to text 48 and identifies the meaning or intent of what the user is saying.

The mental state determination 52 analyzes (a) the tone of the user's voice and (b) the intent as identified by the natural language understanding 50 of the words they are using and (c) event data and compares the tone, intent and event data with models of different mental states such as stressed, agitated, distracted and so forth, in order to identify the likely current mental state of the user.

The historian 54 records the mental state of the user over time. The historian may also record other time series data such as key events, for example, heart rate increasing, over time.

The alerts 56 is a set of text scripts intended to calm the users and direct them to a clearer state of mind. The alerts 56 may include phrases that are tagged with meta data indicating the tone to take, such as stem or calming, which influences the way the text script is spoken to the user. The text script may be translated into speech by the speech to text 48 functionality of the cognitive system 40. The alerts 56 may also include nonverbal dialogs such as haptics (vibration) or playing tones. All of the alerts 56 may be provided to the user to drive the user to respond in an appropriate manner to the impending emergency, disaster or medical situation.

The alerts 56 may be provided to the user through the speaker 26 in the wearable wrist band 14. The alerts 56 may be provided to the user through other wearable devices such as wearable chest band 12. Moreover, the alerts 56 may be provided to the user through other devices such as a haptic interface, point-of-care device, mobile phone, smart watch or augmented reality interface.

A "haptic device" is a device that allows the user to interact with it through the sense of touch. A haptic device recreates the sense of touch by applying forces, vibrations or motions to the user. For example, a mobile phone on vibrate is a haptic device.

A "point-of-care device" is a device that provides a medical service to the user at the point-of-care. Point-of-care is the location wherever a medical service is provided to a user. For example, the point-of-care location could be at a doctor's office or the hospital where the user is treated, could be somewhere out and about in the field through a portable device such as an epi-pen and in general, could be any location where a medical treatment is administered on the spot to a user.

Moreover, the alerts 56 may also be an invoking of external services, for example a geospatial navigation system such as Google maps, and providing these external services to the user if the wearable device 12, 14 identifies the user is stressed because the user is lost.

Figure 5:
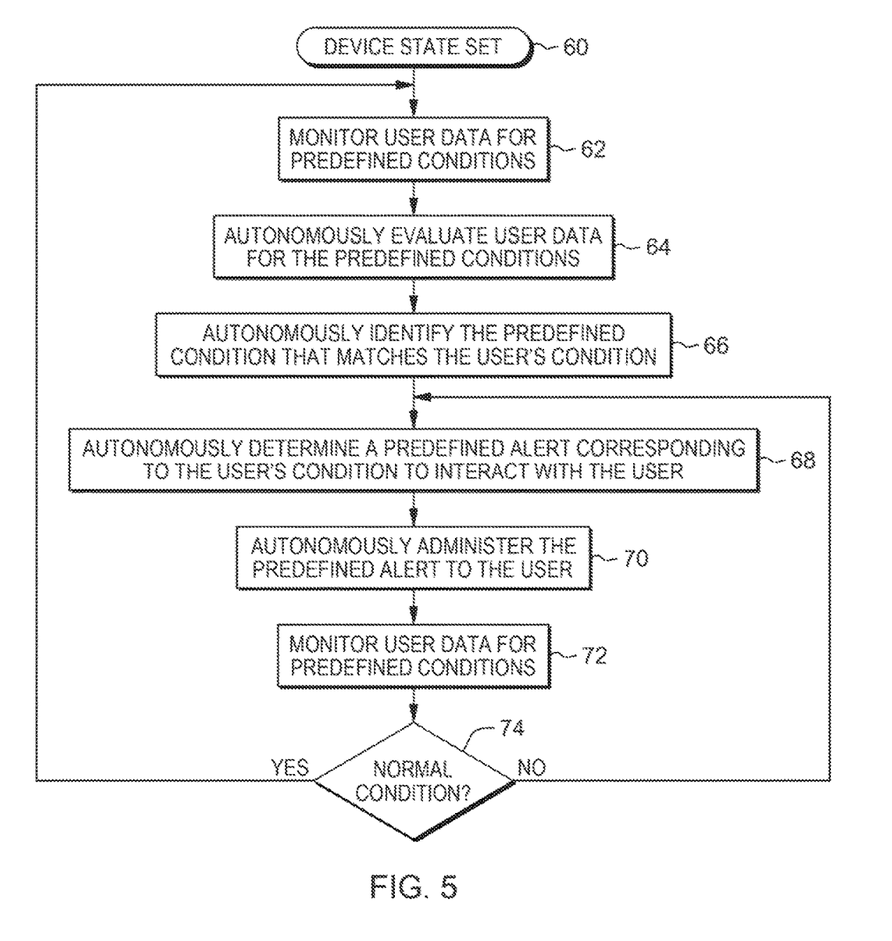
FIG. 5 is a flow chart of a method of the exemplary embodiments.

An exemplary embodiment of a method for providing an alert to a user is indicated in FIG. 5. The state of the wearable device 12, 14 is set, box 60. The wearable device 12, 14 may be set to "active" to begin the process. Setting the wearable device 12, 14 to "active" may be done manually by the user and/or may be set automatically by a broadcast signal. For example, the broadcast signal may be an emergency broadcast signal that indicates that a fire is near.

User data from the user is monitored for predefined conditions, box 62. The user data is that data that is gleaned from the various vital sign, biometric parameter and environmental sensors worn by the user. At least one of the predefined conditions pertains to a mental state of the user The user data is autonomously evaluated for the predefined condition that matches the user's condition, box 64. Of particular concern is the user's mental state.

The predefined condition is autonomously identified that matches the user's condition, box 66.

A predefined alert corresponding to the user's condition is autonomously determined to interact with the user, box 68.

The predefined alert is autonomously administered to the user, 70. The predefined alert may be one of the alerts 56 in the cognitive system 40. The alert may be, for example, a spoken dialog from the speaker 26 of any wearable device, a haptic (vibration) message delivered by a haptic interface in any wearable device or playing tones from the speaker 26 of any wearable device. In addition, other alerts may include a phone call placed to the user, medication delivered to the user via any wearable device, a phone call or other type of message placed to another user of choice, identifying and monitoring and contacting others in the area to see if they also require assistance or are in a position to assist or combination of all or a subset of the foregoing.

Subsequently, user data from the user is monitored for predefined conditions, box 72, to see if the administered alert had any effect on the user.

If a review of the monitored user data in box 72 indicates that the user has returned to a normal condition, box 74, as, for example, the user's vital signs return to normal, the process takes the "YES" path and returns to normal monitoring of the user data for predefined conditions, box 62.

If a review of the monitored user data in box 72 indicates that the user has not returned to a normal condition, box 74, as, for example, the user's pulse rate remains elevated, the process takes the "NO" path and returns to autonomously determine another predefined alert to interact with the user, box 68. It may be that the user's condition is determined to be serious such that a third party, such as emergency medical services, is alerted to the user's condition.

An aspect of the exemplary embodiments is that the cognitive system 40 operates autonomously. That is, the cognitive system is able to operate under the command of the wearable devices 12, 14 without intervention of a third party to evaluate the user data, identify the predefined condition and determine the predefined alert and may even autonomously administer the predefined alert.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It will be apparent to those skilled in the art having regard to this disclosure that other modifications of the exemplary embodiments beyond those embodiments specifically described here may be made without departing from the spirit of the invention. Accordingly, such modifications are considered within the scope of the invention as limited solely by the appended claims.

What is claimed is:

1. A system for providing an alert to a user comprising:
   at least one sensor for sensing user data pertaining to a user's condition;
   at least one non-transitory storage medium that stores instructions; and
   at least one processer that executes the instructions to:
   monitor the user data from the at least one sensor for predefined conditions, at least one predefined condition pertaining to a mental state of the user;
   autonomously evaluate the user data for the predefined conditions;
   autonomously identify the predefined condition that matches the user's condition;
   autonomously determine a predefined alert corresponding to the predefined condition and to the user's condition to interact with the user to calm the user; and
   autonomously administer the predefined alert to the user.

2. The system of claim 1, wherein the user data includes user medical data and environmental data in proximity to the user.

3. The system of claim 1, wherein there are a plurality of sensors, at least one sensor senses user medical data and at least one sensor senses environmental data in proximity to the user.

4. The system of claim 1, further comprising a microphone and wherein the at least one processing unit further executes the instructions to translate speech input to the microphone to text and to understand a meaning or an intent of the speech.

5. The system of claim 4, wherein autonomously identify the predefined condition includes to determine a mental state of the user by a tone of a voice of the user, the meaning or intent of the speech and an analysis of the user data compared with models of different mental states.

6. The system of claim 5, wherein the at least one processing unit further executes the instructions to record the mental state of the user over time.

7. The system of claim 5, further comprising a speaker and wherein to administer the predefined alert includes predefined text scripts to play through the speaker to the user to calm the user.

8. The system of claim 1, wherein the system is wearable.

9. The system of claim 1, further comprising autonomously providing an alert to a third party.

10. A computer implemented method for providing an alert to a user comprising:
- monitoring user data from the user for predefined conditions, at least one predefined condition pertaining to a mental state of the user;
- autonomously evaluating the user data for the predefined conditions;
- autonomously identifying the predefined condition that matches the user's condition;
- autonomously determining a predefined alert corresponding to the predefined condition and to the user's condition to interact with the user to calm the user; and
- autonomously administering the predefined alert to the user.

11. The computer implemented method of claim 10, wherein the user data includes user medical data and environmental data in proximity to the user.

12. The computer implemented method of claim 10, further comprising translating speech received from the user to text and understanding a meaning or an intent of the speech.

13. The computer implemented method of claim 12, wherein autonomously identifying the predefined condition includes determining a mental state of the user by a tone of a voice of the user, the meaning or intent of the speech and an analysis of the user data compared with models of different mental states.

14. The computer implemented method of claim 13, further comprising recording the mental state of the user over time.

15. The computer implemented method of claim 13, wherein administering the predefined action includes playing predefined text scripts to the user to calm the user.

16. A computer program product for providing an alert to a user comprising a computer readable storage medium having program instructions embodied therewith, the program instructions executable by a processor to cause the processor to perform a method comprising:
- monitoring user data from the user for predefined conditions, at least one predefined condition pertaining to a mental state of the user;
- autonomously evaluating the user data for the predefined conditions;
- autonomously identifying the predefined condition that matches the user's condition;
- autonomously determining a predefined alert corresponding to the predefined condition and to the user's condition to interact with the user to calm the user; and
- autonomously administering the predefined alert to the user.

17. The computer program product of claim 16, wherein the user data includes user medical data and environmental data in proximity to the user.

18. The computer program product of claim 16, further comprising translating speech received from the user to text and understanding a meaning or an intent of the speech.

19. The computer program product of claim 18, wherein autonomously identifying the predefined condition includes determining a mental state of the user by a tone of a voice of the user, the meaning or intent of the speech and an analysis of the user data compared with models of different mental states.

20. The computer program product of claim 19, wherein administering the predefined action includes playing predefined text scripts to the user to calm the user.

\* \* \* \* \*